United States Patent [19]
Griesbeck et al.

[11] Patent Number: 5,729,340
[45] Date of Patent: Mar. 17, 1998

[54] BOTTLE INSPECTION MACHINE

[75] Inventors: Karl Griesbeck, Regensburg; Franz Häring, Neutraubling; Wolfgang Ruppelt, Beratzhausen; Hermann Kronseder, Regensburger, all of Germany

[73] Assignee: Krones AG Hermann Kronseder Maschinenfabrik, Neutraubling, Germany

[21] Appl. No.: 406,911

[22] PCT Filed: Jul. 29, 1994

[86] PCT No.: PCT/EP94/02523

§ 371 Date: Mar. 27, 1995

§ 102(e) Date: Mar. 27, 1995

[87] PCT Pub. No.: WO95/04267

PCT Pub. Date: Feb. 9, 1995

[30] Foreign Application Priority Data

Jul. 30, 1993 [DE] Germany ................ 93 11 405 U
Sep. 1, 1993 [DE] Germany ................ 93 13 115 U

[51] Int. Cl.⁶ ..................................... C01N 21/32
[52] U.S. Cl. ............... 356/240; 250/223 B; 348/127
[58] Field of Search .................... 356/240, 428; 250/223 B; 348/127

[56] References Cited

U.S. PATENT DOCUMENTS

| | | | |
|---|---|---|---|
| 3,932,042 | 1/1976 | Faani et al. | 356/240 |
| 4,025,201 | 5/1977 | Deane | 356/240 |
| 4,280,624 | 7/1981 | Ford | 356/240 |
| 4,376,951 | 3/1983 | Miyazawa | 250/223 B |
| 4,500,203 | 2/1985 | Bieringer | 250/223 B |
| 4,509,081 | 4/1985 | Peyton et al. | 250/223 B |
| 4,586,080 | 4/1986 | Hoyt et al. | 358/106 |
| 4,691,231 | 9/1987 | Fitzmorris et al. | 250/223 B |
| 4,958,223 | 9/1990 | Juvinall et al. | 348/127 |
| 5,256,871 | 10/1993 | Baldwin | 356/240 |

FOREIGN PATENT DOCUMENTS

0037694 10/1981 European Pat. Off.
3035077 4/1982 Germany ................ 356/240

*Primary Examiner*—Richard A. Rosenberger
*Attorney, Agent, or Firm*—Ryan, Maki, Mann & Hohenfeldt, S.C.

[57] ABSTRACT

An inspection machine for transilluminatable bottles inspects the sidewalls of bottles by transmitting a diffused beam of light through the sidewall and using a plurality of mirrors appropriately arranged for detecting or recording the images emergent from the bottle in different directions in the same image recording camera. The arrangement requires at least two separate beam paths and mirrors in each path directing the bottle emergent beams to the camera while the bottles are being conveyed through a position in which they are illuminated. In an improved arrangement, there is a separate cooperating series of beam deflecting mirrors which generate at least three independent beam paths that impinge from different directions on the sidewall of the bottle being inspected. The recording device is preferably a camera having a charge coupled device image plate.

22 Claims, 7 Drawing Sheets

BOTTLE INSPECTION MACHINE

BACKGROUND OF THE INVENTION

The invention disclosed herein pertains to a machine for inspecting bottles or the like through which light can be transmitted.

In beverage bottling lines inspection machines are used to detect and eliminate damaged or dirty bottles before they reach a bottle filling machine. Most pre-existing bottle filling machines require rotation of each bottle about its vertical axis while a thin vertically extensive light beam passes through the bottle for a projected image of the bottle sidewalls to be recorded. During rotation, substantially only the center of the bottle is currently recorded along a vertical line. A line scan camera may be used. The image of the bottle sidewall obtained is of sufficient quality to reveal or detect bottles that are damaged or dirty. In the pre-existing machine just outlined, rotation of the bottles as they arrive in the inspection zone requires that the bottles be mounted on rotationally driven plates that are carried on a carousel that has the mechanism for rotating the plates. This is a complicated and expensive structural arrangement which it would be desirable to avoid.

There is existing inspection apparatus which does not require rotation of the bottle during image recording of the sidewall as is disclosed in German specification DE-AS 26 17 457. In the patented apparatus, the sidewall region of the bottle is recorded by only one camera that views the bottle from different directions. This bottle inspection apparatus is of comparatively simple design but is subject to causing optical distortions due to the surface curvature of the bottles. With this arrangement, evaluation of the image for the presence of dirt or damage is difficult and uncertain.

SUMMARY OF THE INVENTION

The invention disclosed herein is an improvement over the inspection apparatus outlined in the preceding paragraphs. According to the invention, a machine for inspecting the sidewall of bottles or the like is achieved and implemented at comparatively low cost although the resulting images of the bottles are of good quality.

The improved bottle inspection apparatus uses an arrangement of mirrors which direct a plurality of individual beam paths that emerge from the sidewall region of a bottle that is transilluminated over its entire width through an image recording device such as a camera that has a charge coupled device (CCD) image plate. The arrangement ensures that the images projected to the camera by the individual beam paths are of identical size such that difficulties in image interpretation or evaluation are eliminated. The bottle wall inspection station can also be associated, in accordance with the invention, with an additional image recording device, such as another CCD camera, for checking the contour, type or color of the bottles that traverse the second inspection station. The second image recording device can be positioned so that its beam path intersects the beam paths of the sidewall inspection arrangement such that recording of both images can advantageously be triggered with only one camera triggering device.

How all of the foregoing general features and other more specific features of the invention are achieved and implemented will appear in the more detailed description of a preferred embodiment of the invention which will now be set forth in reference to the accompanying drawings.

DESCRIPTION OF A PREFERRED EMBODIMENT

Figure 1:
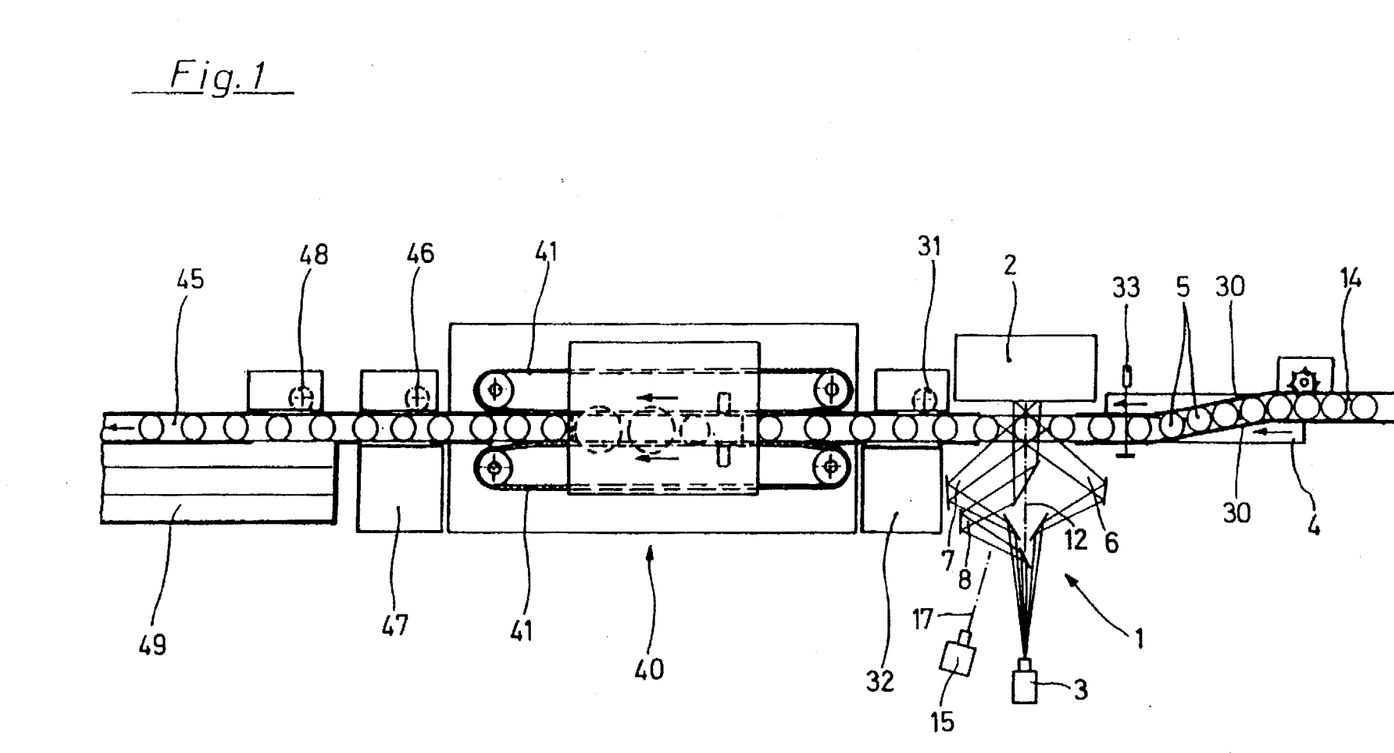
FIG. 1 is a diagrammatic top plan view of a machine for inspecting bottles wherein the new sidewall inspection apparatus is used.

Referring to FIG. 1, bottles 5 are conveyed to the inspection machine on an infeed conveyor 14 which is driven continuously. The bottles 5 are transported in upright position on conveyor 14, the bottles being in abutting position at that time. Conveyor 14 may be a belt conveyor or a conveyor comprised as a series of plates that are linked together to form a closed loop. The bottles must be spaced from each other when they arrive at the inspection station 1. Accordingly, a pair of angulated guide rails guide bottles 5 onto a conveyor 4 which has a higher linear velocity than conveyor 14 so that a uniform width space is developed between consecutive bottles when they are passing through inspection station 1 on conveyor belt 4. Inspection station 1 comprises a luminescent screen emitting diffused light, a camera 3 which records an image of the bottle and several mirrors disposed between conveyor belt 4 and camera 3 for directing light beams which entrain the image of the bottle from the bottle to the camera 3. The beam paths are marked 6, 7 and 8. Inspection station 1 includes a second camera 15 for detecting the contour, height and/or color of the bottles being inspected. The length of the beam path from the bottle 5 being inspected to the camera can be very short such as between 750 mm and 1500 mm. It has been found desirable to use a combination of mirrors and optical properties of the camera which provides for a beam path length of about 1240 mm.

Bottles that fail sidewall inspection or contour, height and/or color inspection are automatically ejected by actuation of ejection device 31 when any unacceptable bottle becomes aligned with ejection device 31. A container 32 is provided for collecting unacceptable bottles which are ejected. Ejector devices are well known and need not be described in great detail. Basically, the ejector device 31 is activated at the end of a time delay interval which allows the unacceptable bottle to travel the distance from the inspection zone to the ejector device. Triggering the two cameras 3 and 15 and ejection device 31 occurs when a bottle 5 cuts the light beam of a photodetector 33 which precedes inspection station 1 and which takes into account a delay interval whose length depends on the speed of bottle conveyance.

A second inspection station, designated generally by the numeral 40, is arranged downstream from the ejector device. Second inspection station 40 provides for inspecting the bottoms of the bottles. Bottom inspection requires that the bottom of the bottle be free of any supporting member. There is a gap between bottle feed conveyor 4 and output conveyor 45. The bottles are transported across this gap by endless belts 41 which frictionally engage the sidewall of a bottle and carry it though space with its bottom exposed. The bottles are released from friction belts 41 to outfeed conveyor 45 after they have traversed the gap between conveyors 4 and 45. Another ejection device 46 is positioned as shown in FIG. 1 for ejecting bottles which have failed bottom inspection. Ejector 46 ejects unacceptable containers into a collecting container 47. There is also a third ejection device 48 which shifts bottles which are potentially reusable after repeated cleaning onto a conveyor 49 which is arranged parallel with the outfeed conveyor belt 45.

Figure 2:
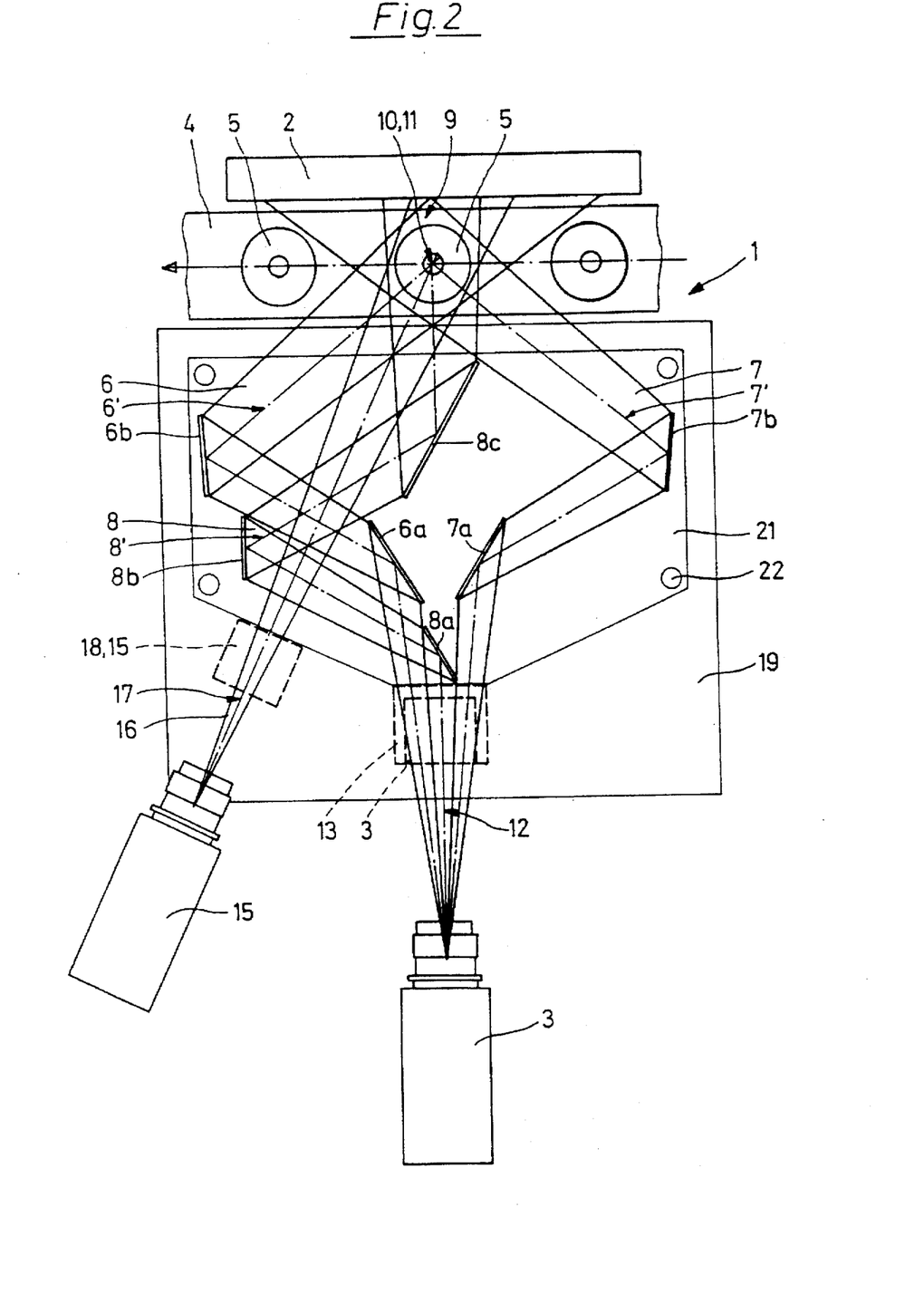
FIG. 2 is an enlarged representation of the bottle sidewall inspection apparatus that is shown in more demagnified form in FIG. 1.

Attention is now invited to FIG. 2 which depicts an enlarged version of inspection station 1. In FIG. 2, light emitted from diffuse light source 2 penetrates from one side of bottle 5 through the bottle to define a beam 6 in which an image of the bottle is entrained. In other words, the wall of the bottle or any defects or contaminants in it modulate light beam 6. Another light beam 7 also entrains an image of the bottle. The beams or the beam paths are arranged symmetrically to the optical axis 12 of camera 3. Thus, the mirrors 7a and 7b forming the beam path 7 are positioned symmetrically to the mirrors 6a and 6b of the beam path 6. The two mirrors 6b and 7b are oriented with respect to each other such that the beam path 6 and 7 meet at a given angle, for example, 60°, relative to the center lines 6' and 7' of the beam paths in an intersecting region above conveyor belt 4. A third more centralized beam path directs the image that emerges from bottle 5 through the sequence of reflecting mirrors 8c, 8b and 8a in that order to the optical axis 12 of camera 3. In the third beam path, the center line or center axis 8' of third beam 8 bisects the angle between the two center axes 6' and 7'. Mirror 8c is positioned so that the perpendicular projection of center axis 8' in FIG. 2 is oriented on the common point of intersection 10 of the three axes 6', 7' and 8' normal to the line of symmetry 11 of the bottle 5 being inspected and also to the running duration of conveyor belt 4.

Sidewall inspecting camera 3 is provided with an image plate not visible comprised of charge coupled devices (CCD) on which the images transmitted along the three beam paths 6, 7 and 8 are formed one next to the other. There is an evaluation device, not shown, which under program control reads and evaluates images recorded by camera 3. The evaluation program is preferably designed so that only the center image of each beam path is evaluated while the margin areas can be masked to some extent or can be ignored in order to avoid imprecisions in the margin areas of the recorded areas due to the optical distortions on the sharply curved bottle edges.

As previously mentioned, inspection station 1 includes a second camera 15 for inspecting the contour and/or height and/or color of the bottles to be inspected. Second camera 15 is disposed so that the beam path 16 is not obstructed in whole or in part by any of the mirrors from the sidewall inspection device that utilize camera 3. Camera 15 intercepts an image of the bottle 5 which is presently positioned in the intersection region of the other beams 6, 7 and 8. In particular, the optical axis 17 of camera 15 is oriented so that it extends to a common point of intersection 10 with the three beam paths 6, 7 and 8 of the sidewall inspection beams. This arrangement permits operating the two cameras 3 and 15 with a common control signal for simultaneous image recording. It will be evident in FIG. 2 that camera 15 could be shifted slightly to the left or to the right without the beam which the camera intercepts being obstructed with any of the mirrors 6a, 8b or 8c. A desirable arrangement is where the optical axis 17 of the camera 15 beam path 16 intersects the axis 8' or the optical axis 12 of camera 3 at an angle of approximately 25°.

Instead of the cameras 3 and 15 having their optical axes 12 and 17 projected horizontally, the cameras can be arranged with their axes vertical and perpendicular to the plane in which the bottles are conveyed. To effectuate this arrangement, additional mirrors 13 and 18 are required for bending the horizontal beam paths 7 and 8 for camera 3 and beam path 16 for camera 15 so the image information beams can be received in the cameras along their vertically arranged axes.

Figure 3:
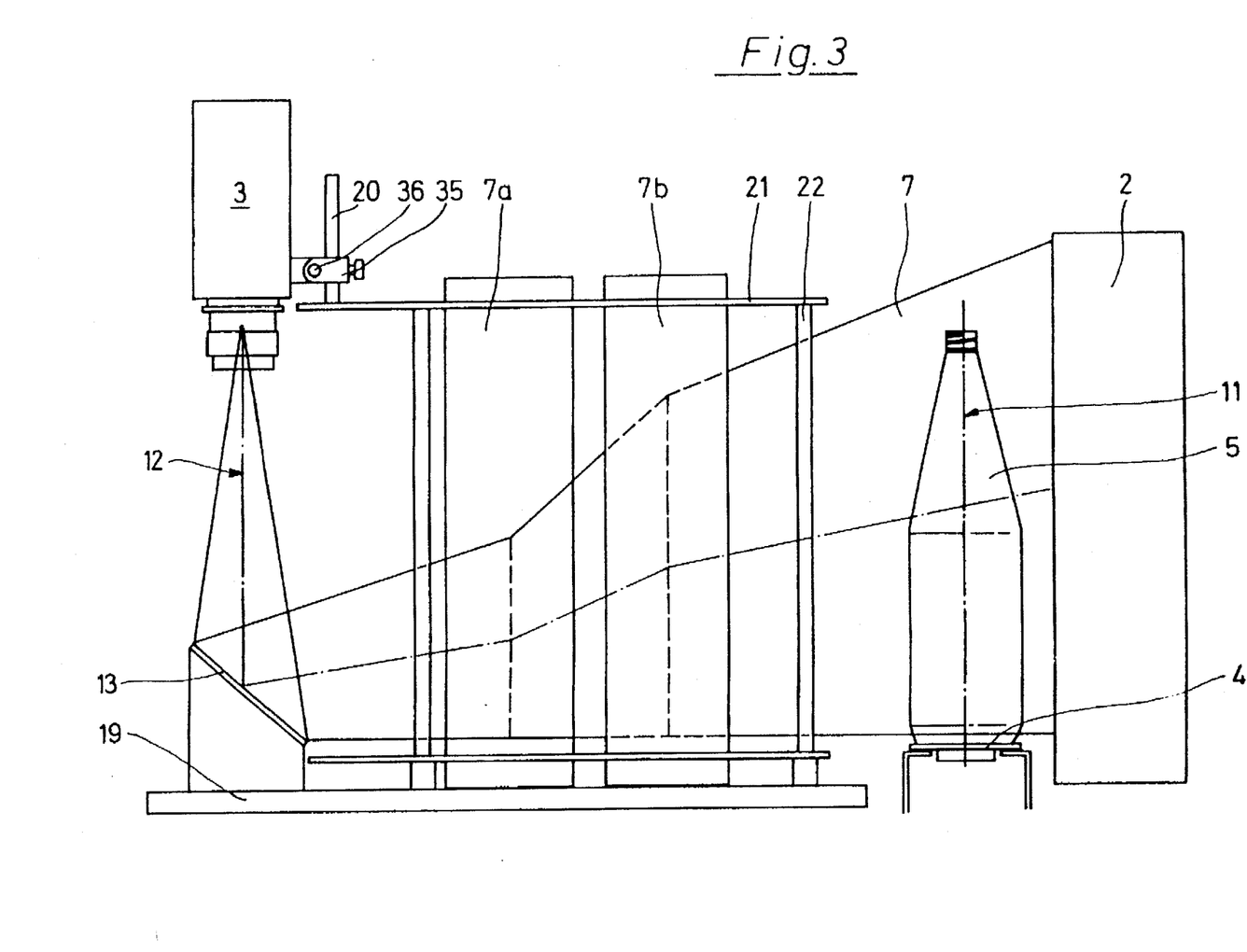
FIG. 3 is a diagrammatic side elevational view of one of the beam paths extending from a luminescent screen to a camera that is depicted in reduced size in FIG. 1.

In FIG. 3, for the sake of greater clarity, only the camera 3 and the two mirrors 7a and 7b in the beam path 7 are shown in a side view. The beam path of the center axis denoted by 7' is shown in FIG. 2. Positioning of the planar mirrors 7a and 7b (and also positioning of the remaining mirrors) takes place through two positioning plates marked 21 and arranged parallel to each other and at a distance from each other in a horizontal plane. Plates 21 are fastened to and supported by spacer rods 22 from a base 19. Positioning plates 21 have slots corresponding to the thickness and width of the mirrors. The mirrors can be introduced from above through the slots with their lower edges resting on base plate 19. This permits fast and simple exchange of mirrors if a mirror is damaged.

As shown in FIG. 3, the upper positioning plate 21 is fastened to a guide rod 20. In this figure, camera 3 is arranged with its optical axis 12 vertically oriented. The camera 3 is pivotally connected by means of a pin 36 to a clamping device 35 which allows the camera 3 to be adjusted up or down on rod 30. Clamping device 35 includes a pivotal pin 36 which allows setting the angle of the optical axis of camera 3 centrally of the mirror 13 which is arranged below the camera.

Figure 4:
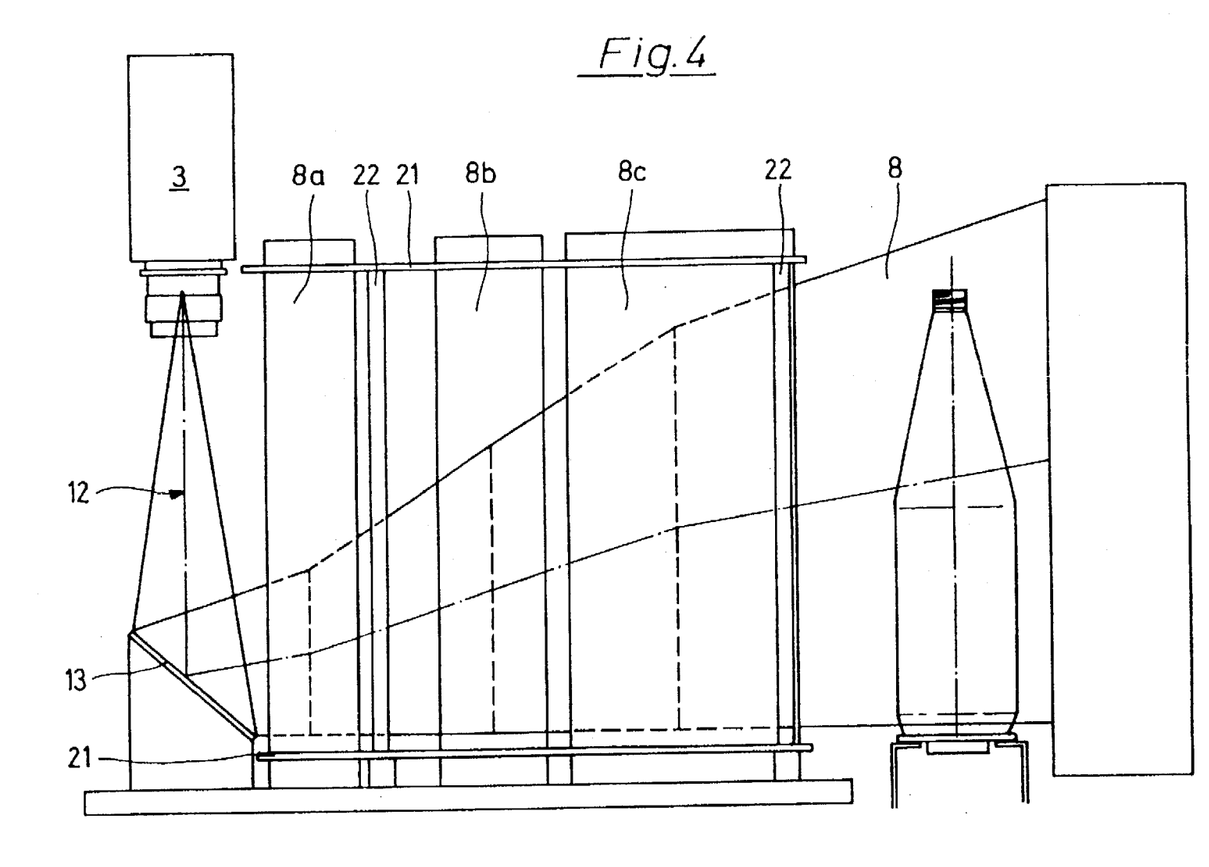
FIG. 4 is a diagrammatic side elevational view of another one of the beam paths that is present in FIG. 2 as viewed in the direction in which the bottles are conveyed.

FIG. 4 is similar to FIG. 3 except that FIG. 4 depicts the mirrors 8a, 8b, and 8c associated with the center beam path 8. As in the previous figure, in FIG. 4 all remaining mirrors are omitted for the sake of clarity.

Figure 5:
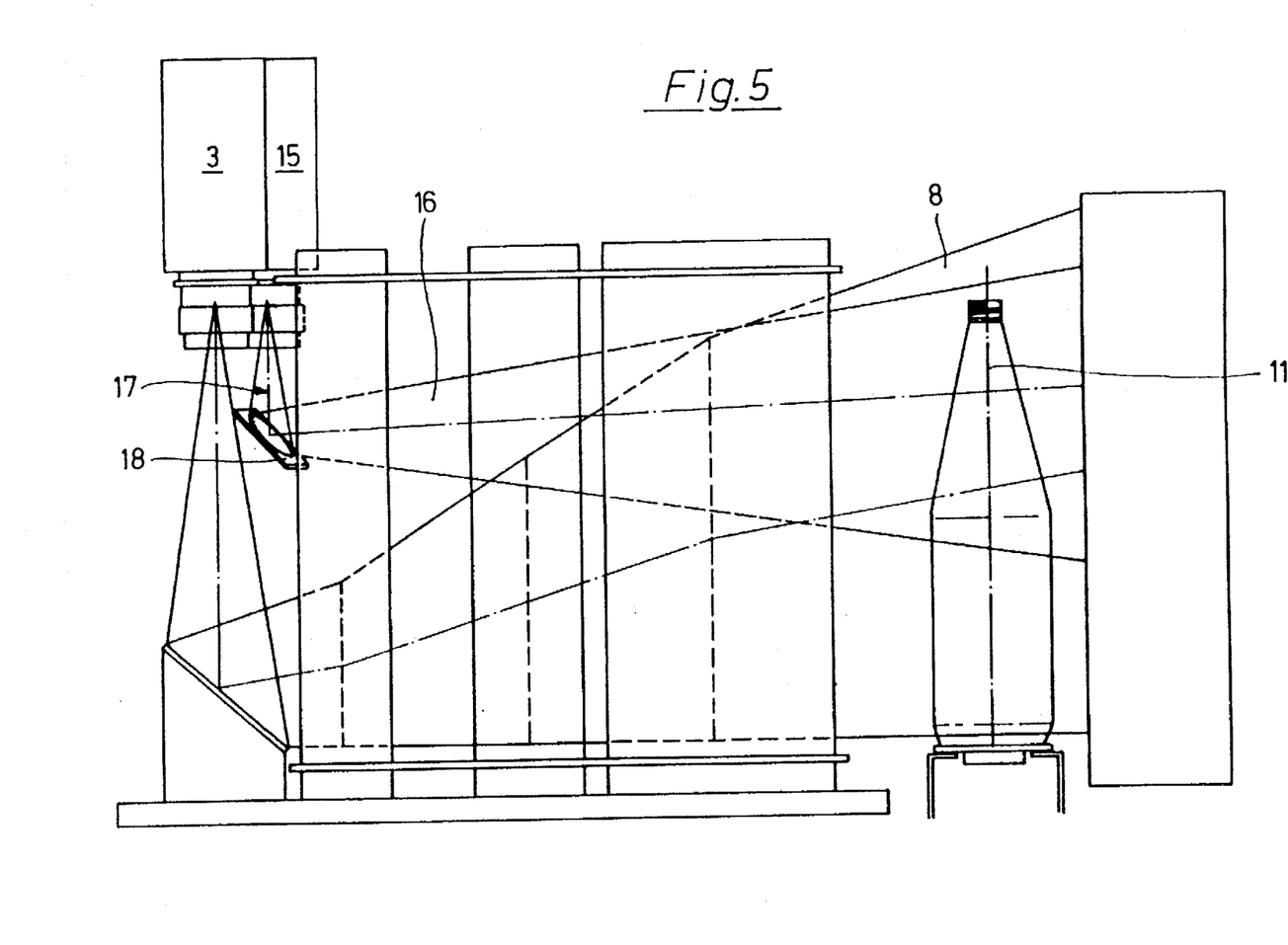
FIG. 5 is a third diagrammatic side elevational view of another of the beam paths present in FIG. 2 as viewed in the direction of bottle conveyance.

FIG. 5 corresponds to FIG. 4 for the most part but with camera 15 and its beam path 16 involved in bottle contour and height detection being added. As previously indicated, because the optical axis of camera 15 is vertically oriented, mirror 18 is required for deflecting beam path 16 from the perpendicular direction transversely to the line of symmetry 11 of the bottle being inspected. The second camera 15, similarly to camera 3, is fastened on the upper positioning plate 21 so as to be adjustable.

Inspection of the shoulder and head region of bottles 5 requires only that the upper region of the bottle be the source of an emergent light beam. This permits having beam path 17 of substantially shorter length than the beam paths for sidewall inspection so the camera 15 can be disposed without an additional deflecting mirror as close to the bottle as the sidewall inspection camera 3.

Figure 6:
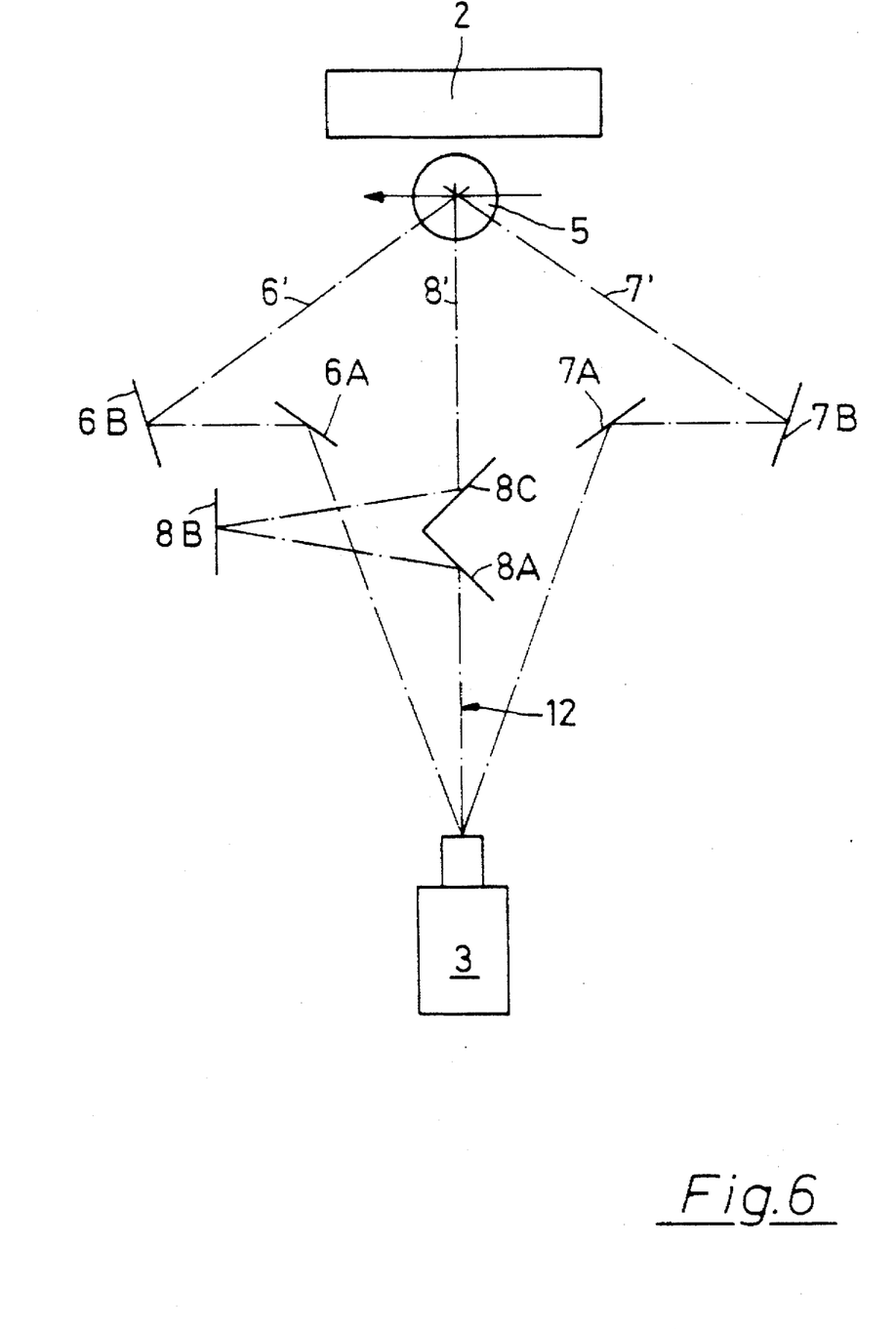
FIG. 6 is a schematic top plan view of an optical system that performs the functions of the FIGS. 1–5 embodiment generally but has the mirrors used in the optical system arranged differently from their arrangement in FIG. 2.

FIG. 6 shows an alternative arrangement for the mirrors involved in directing the modulated light beams emergent from bottle 5 for sidewall inspection. The depicted mirror configuration also defines two beam paths 6 and 7 disposed symmetrically to optical axis 12 of camera 3. Of these beam paths, only the central axis 6' and 7' are shown. For this purpose, mirrors 6A, 6B and 7A and 7B are present which are disposed at a sufficient spacing from the optical axis 12 so that mirrors 8A, 8B and 8C forming the third beam path 8 can be placed in front of the upper mirrors so the other two remaining beam paths so that a segment of the beam path 8 leading to bottle 5 can pass with no obstruction between the mirrors associated with beam paths 6 and 7. It should be understood that the plural beam paths discussed above are not necessarily limited to three beam paths for sidewall inspection. It is conceivable and advantageous to sometimes arrange additional mirrors for developing more than three separate beam paths for sidewall inspection.

An elaboration of the bottle inspection machine discussed above is depicted in the FIG. 7 diagrammatic top plan view of the machine. This machine uses a second inspection station 100 of the type used for sidewall inspection of bottles 5. Inspection station 100 is positioned adjacent outfeed conveyor 45 downstream from the inspection station 40 wherein the bottom of each bottle is inspected. The mirror arrangement in inspection station 100 is the same as the arrangement of the mirrors in inspection station 1. Bottle gripping closed loop belts 41 are driven synchronously with conveyor belts 4 and 45. However, one of the closed loop belts 41 translates at a speed that differs by a small amount from the other belt 41. As a result of the difference in speeds, bottles gripped by the belts are rotated about their vertical axes during transfer from conveyer belt 4 to conveyor belt 45. The angle of rotation is predetermined by the difference in belt speeds but the speed difference is preferably chosen so that each bottle is rotated about 90° about its vertical axis without being tilted. Elimination of unusable or rejected bottles 5 is achieved using a conventional ejector such as was used in FIG. 1 embodiment.

Figure 7:
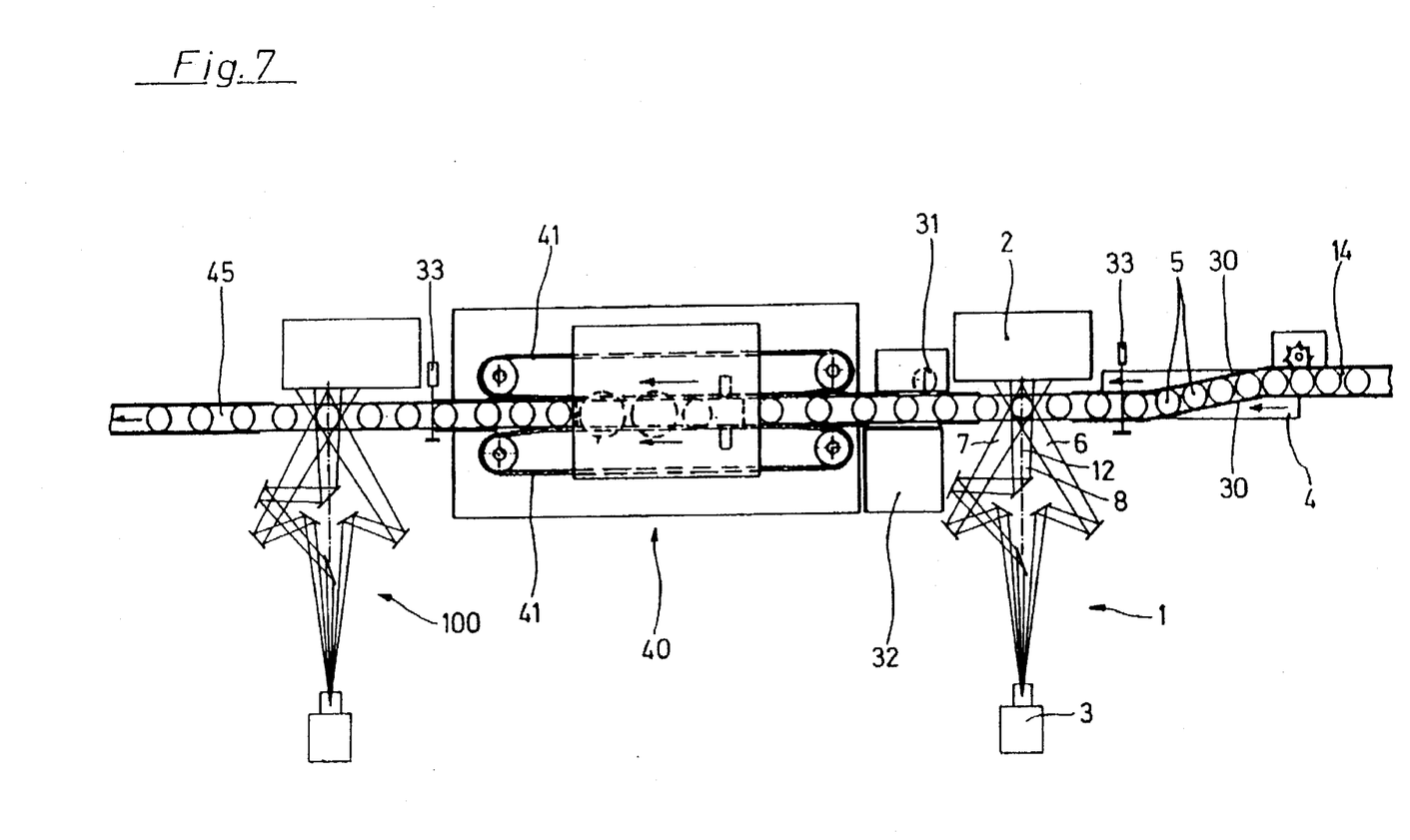
FIG. 7 is a diagrammatic plan view in which there are two inspection stations of the bottle sidewall inspecting types used.

As stated, the speed difference between the two belts 41 is adjustable so that when converting the inspection machine to bottles with a difference circumference, the rotational angle of the bottles is held at a constant 90° during traversing the space or gap between conveyor belts 4 and 45. For this purpose, one of the belts 41 can be positively engaged with the drive, not shown, for conveyor belts 4 and/or 45 while the other belt is regulated under the influence of a programmable controller, not shown, to adjust for different bottle diameters or circumferences. Altering the ratio of transmission between the two belts can be achieved simply by sending a signal to the controller by means of a push button switch.

A sidewall inspection with two inspection stations 1 and 100 as in FIG. 7 has the advantage of the spacing between the bottles in the bottle stream being kept small and the speed at which the bottles are transported at a given power level is lower than is the case with an inspection of the total bottle sidewall with only one inspection station. This accomplishment results from the smaller angle which can be selected between beams 6 and 7. For example, the angle may be as little as 60° since the bottle sidewall when passing one of the inspection stations 1 and 100 does not need to be recorded with its full circumference. By way of the small angle, optical advantages are obtained during image recording. When only a single inspection station is used for sidewall inspection, an angle of more than 100° is required between beams 6 and 7 for complete inspection of a bottle wall.

We claim:

1. Apparatus for inspecting transilluminatable bottles comprising:
 a source of light arranged on one side of a bottle that is positioned for being transilluminated in at least three directions by light emanating from said source,
 a single camera positioned at a side opposite of the bottle from said source of light, said camera having an optical axis that is directed to the axis of symmetry of a bottle that is positioned for being inspected and the axis of symmetry of the bottle and said optical axis of the camera are intersected by a common imaginary plane,
 first and second beams that contain images of the bottle respectively, after having passed through the bottle have their paths from the bottle to said camera defined, respectively, by first and second mirror systems where the mirror systems and the beams reflected thereby are symmetrical to opposite sides of said plane,
 a third beam that contains an image of the bottle after having passed through the bottle has its path from the bottle to said camera defined by a third mirror system arranged between said two mirror systems,
 each of said first, second and third images that are contained in the beams defined by the respective mirror systems have a central axis which intersect each other and said axis of symmetry of the bottle in a common point, and
 the lengths of said central axes of the beams from said common point of intersection to said camera are equal.

2. Apparatus according to claim 1 including:
 a conveyor for conveying bottles in succession into said position for undergoing inspection,
 each of the beams having an axis and all of the axes intersecting the axis of a bottle when said bottle is positioned for undergoing inspection.

3. Apparatus according to claim 1 wherein each of said beams (6, 7, 8) defined by said mirror systems have central axes (6', 7', 8') respectively, said central axes intersecting each other at a common point (10) within a bottle positioned for being inspected, said central axes also intersecting the axes of symmetry (11) of a bottle when it is positioned.

4. Apparatus according to claim 1 wherein the said axes of the beams defined by said mirror systems have equal lengths between 750 mm and 1500 mm.

5. Apparatus according to claim 1 wherein the lengths of said axes of the beams defined by the mirror systems are all equal to substantially 1240 mm.

6. Apparatus according to claim 1 wherein said optical axis of said camera is substantially perpendicular to the direction in which the bottles are conveyed by said conveyor to the position for being inspected.

7. Apparatus according to claim 1 wherein said axes of the beams that contain images of a bottle and are defined by said mirror systems are directed horizontally,
 said camera is arranged such that its optical axis is directed vertically and including:
 a mirror to which the axes of all of said beams and the optical axis of the camera are directed, said last named mirror being set in an angular attitude appropriate for reflecting and changing the direction of the axes of the beams and the axes of the camera from horizontal to vertical for the axes of the beams and optical axis of the camera to be coincident at the camera.

8. Apparatus according to claim 1 wherein:
 one of said two beams that contains an image of the bottle defined by a mirror system is defined by two cooperating mirrors (6a, 6b) disposed between the bottle and the camera and the other one of the two beams that contains an image of the bottle is defined by two cooperating mirrors (7a, 7b) disposed between the bottle and the camera and arranged to reflect said two beams away from the axis of symmetry,
 the mirror arrangement in each of said two systems that include mirrors (6a, 7a) reflecting beams (6, 7), respectively, in directions away from said plane of symmetry such that said mirrors (6b and 7b) reflect said beams (6, 7), respectively, toward said plane of symmetry.

9. Apparatus according to claim 8 wherein said camera is oriented such that its optical axis is directed horizontally at a level above the level of a horizontal plane along which the bottle is moved to arrive at the position for being inspected.

10. Apparatus according to claim 8 wherein each of said two beams have a central axis (6',7') and the angle between each axis and said plane of symmetry is between 45° and 80°.

11. Apparatus according to claim 10 wherein said angle is about 60°.

12. Apparatus according to claim 8 including a second camera (15) spaced from camera (3), the second camera arranged to record a beam containing information about any one or all of the contour, height and color of a bottle (5) positioned for inspection, the optical axis of said second camera extending through a common point of intersection of the axis of symmetry of the bottle the central axes (6',7',8') of the three beams (6,7,8) and the optical axis of the first camera (3).

13. Apparatus according to claim 12 wherein the optical axis (12) of the sidewall inspection camera (3) is directed from the camera (3) to be intercepted and deflected by one mirror (8a) disposed on a line directed to said line of symmetry (11) and said mirror (8a) redirects said optical axis (12) laterally across the optical axis (17) of second camera (15) to another mirror (8b) whereby the optical axes (12, 17) of the sidewall inspection camera (3) and the second camera 15 cross with an acute angle between them of about 15° to 35°.

14. Apparatus according to claim 13 wherein said acute angle is preferably equal to about 25°.

15. Apparatus according to claim 1 wherein:

said third mirror system includes three mirrors (8c, 8b, 8a), one of said mirrors (8c) in the third system is disposed substantially on said plane of symmetry for said defining of said beam containing a third image of a bottle positioned for being inspected, said mirror (8c) is arranged to reflect said beam containing said third image in a direction away from said plane of symmetry to a mirror (8b) positioned laterally away from said plane of symmetry, and said mirror (8b) is arranged for reflecting said third image generally toward said plane of symmetry to a mirror (8a) positioned substantially on said plane of symmetry and arranged for reflecting said third beam along said plane into the camera.

16. Apparatus according to claim 15 wherein the optical axis of said camera is directed vertically and an additional mirror (13) is positioned for receiving the three beams containing, respectively, an image of a bottle in inspection position, said additional mirror is arranged for changing the direction of the beams from horizontal to vertical for the axes of the three beams to enter the camera coincident with the optical axis of the camera.

17. Apparatus according to claim 1 including a base plate (19) on which the mirrors in said mirror systems are mounted for standing, and a mirror positioning plate (21) arranged parallel to the base plate, said positioning plate having slots into which the mirrors extend.

18. Apparatus according to any one of claims 15, 16, or 12 wherein said camera (3) has a photosensitive image plate and individual images defined by said mirrors are formed separately from each other and next to each other on the image plate.

19. Apparatus according to claim 18 wherein said image plate is a charge coupled device matrix.

20. Bottle inspection machine having first and second inspection stations (1,100) each including structure defined in claims 9 or 15, bottles to be inspected being conveyed through the first inspection station (1) and then downstream through second inspection station (100), and a device positioned between station (1) and station (100) for turning bottles about their vertical axes through a predetermined angle before they arrive at the second inspection station.

21. A machine according to claim 20 wherein said predetermined angle is about 90°.

22. The machine according to claim 21 wherein said device is comprised of two belts having runs extending parallel to each other and translating in the same direction for gripping a bottle between them, one belt having a translational speed greater than the other to impart rotation to a bottle.

* * * * *